(12) United States Patent
Vipparla et al.

(10) Patent No.: US 11,008,296 B2
(45) Date of Patent: May 18, 2021

(54) INTERMEDIATES FOR THE PREPARATION OF ERIBULIN THEREOF

(71) Applicant: NATCO PHARMA LIMITED, Hyderabad (IN)

(72) Inventors: Bulli Babi Vipparla, Hyderabad (IN); Sreenivas Nagapuri, Hyderabad (IN); Sathaiah Kandula, Hyderabad (IN); Janaki Rama Rao Ravi, Hyderabad (IN); Durga Prasad Konakanchi, Hyderabad (IN); Pulla Reddy Muddasani, Hyderabad (IN); Venkaiah Chowdary Nannapaneni, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 0 days.

(21) Appl. No.: 16/765,664

(22) PCT Filed: Nov. 20, 2018

(86) PCT No.: PCT/IN2018/050765
§ 371 (c)(1),
(2) Date: May 20, 2020

(87) PCT Pub. No.: WO2019/102490
PCT Pub. Date: May 31, 2019

(65) Prior Publication Data
US 2020/0299248 A1    Sep. 24, 2020

(30) Foreign Application Priority Data

Nov. 21, 2017    (IN) .............................. 201741041585

(51) Int. Cl.
*C07D 307/20*    (2006.01)
(52) U.S. Cl.
CPC .................................. *C07D 307/20* (2013.01)
(58) Field of Classification Search
CPC .................................................. C07D 307/20
(Continued)

(56) References Cited

U.S. PATENT DOCUMENTS 6,214,865 B1    4/2001    Littlefield et al.

FOREIGN PATENT DOCUMENTS

WO    WO-2005/118565    12/2005
WO    WO-2015/000070    1/2015

OTHER PUBLICATIONS

International Search Report and Written Opinion for International Patent Application No. PCT/IN2018/050765, dated Feb. 21, 2019 (8 pages).

*Primary Examiner* — Taylor V Oh
(74) *Attorney, Agent, or Firm* — Mintz Levin Cohn Ferris Glovsky and Popeo, P.C.

(57) ABSTRACT

The present invention relates to novel intermediates of Eribulin and process for the preparation of the same. The process of the present invention is commercially viable and can be easily adopted for plant scale operations. The present invention relates to tetrahydrofuran compounds of formula I, X, XI, D and B.

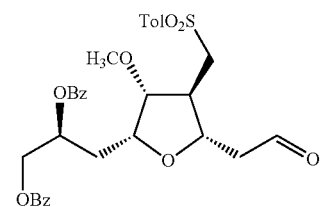

I

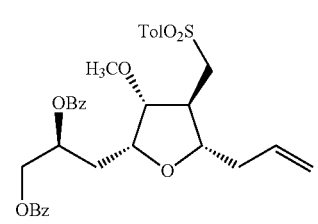

X

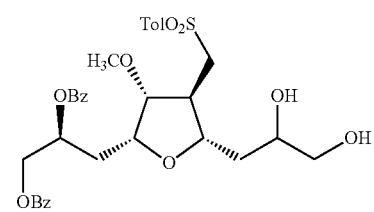

XI

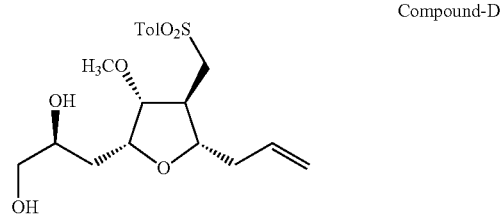

Compound-D (Continued)

-continued
Compound-B
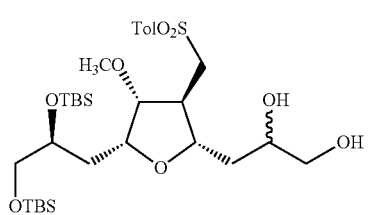
10 Claims, No Drawings
(58) Field of Classification Search
USPC ......................................................... 549/475
See application file for complete search history.

INTERMEDIATES FOR THE PREPARATION OF ERIBULIN THEREOF

FIELD OF THE INVENTION

The present invention relates to novel intermediates of Eribulin and process for the preparation of the same. The present invention involves less expensive reagents, solvents and the process conditions can be easily adopted for commercial scale.

BACKGROUND OF THE INVENTION

Eribulin, is a synthetic macrocyclic analogs of halichondrin B, and is represented by structural formula as shown in below.

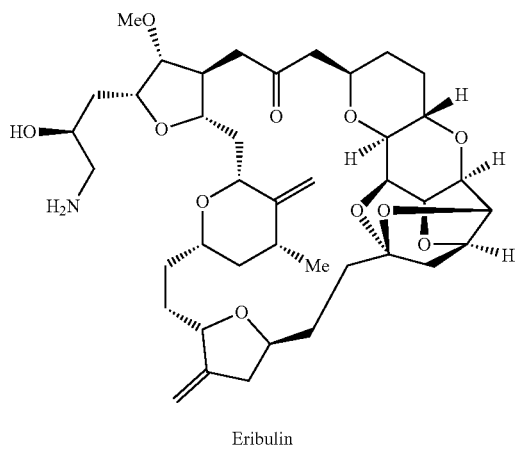

Eribulin

Eribulin is marketed as Eribulin Mesylate under the brand name HALAVEN® and it is indicated for the treatment of patients with metastatic breast cancer. U.S. Pat. No. 6,214,865 discloses Eribulin.

PCT application WO 2005/118565 discloses process for the synthesis of Eribulin. Tetrahydrofuran compound of formula IA is used as one of the intermediate.

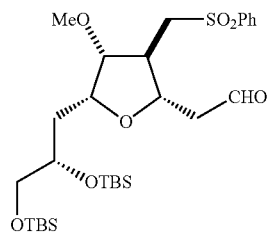

Formula IA

During development of the process, we observed some disadvantageous with the above compound of formula-IA. The final step of the process involves ozonolysis which is not commercially viable, and also observed that degradation of the compound of formula-IA during purification by column chromatography. Accordingly, there is a need for the invention of stable and novel intermediates of Eribulin.

SUMMARY OF THE INVENTION

According to a first aspect of the present invention, there is provided compounds useful in the synthesis of Eribulin.

One aspect of the present invention provides a tetrahydrofuran compound of formula I.

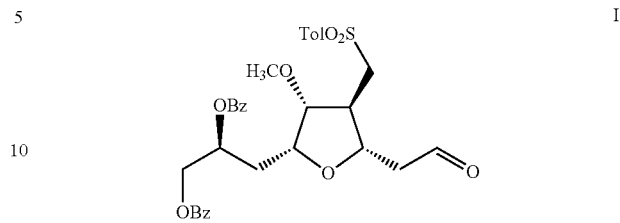

I

Another aspect of the present invention provides a tetrahydrofuran compounds of formula X and XI.

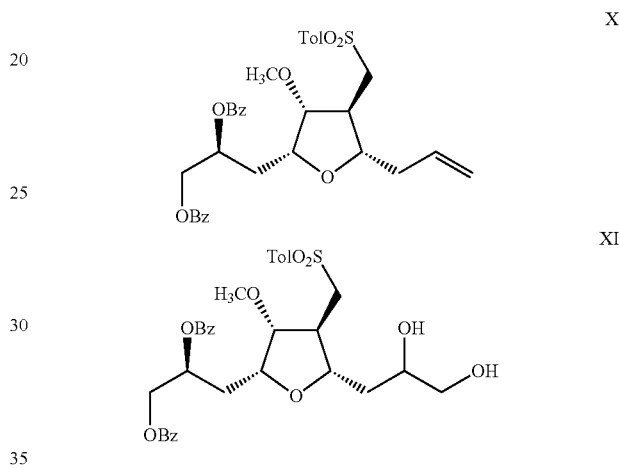

X

XI

Another aspect of the present invention provides a tetrahydrofuran compounds of formula D and B.

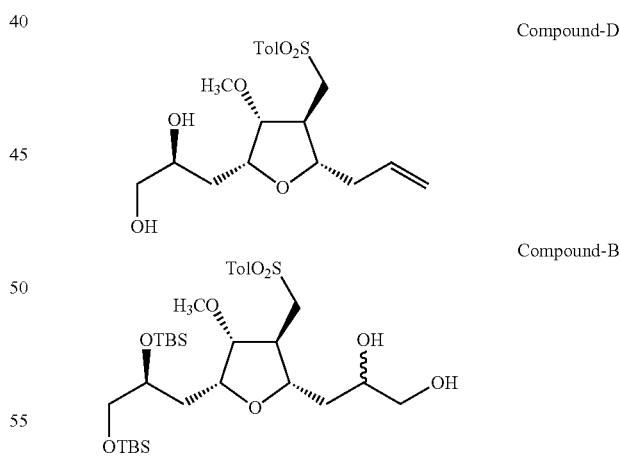

Compound-D

Compound-B

Yet another aspect of the present invention is to provide a process for the preparation of a tetrahydrofuran compound of formula I comprising the steps of:
a) methylating a tetrahydrofuran of formula IX in presence of 1,8-Bis(dimethylamino)naphthalene to get a tetrahydrofuran compound of formula X,
b) dihydroxylating the tetrahydrofuran compound of formula X to get compound of formula XI,
c) oxidizing the compound of formula XI to get a tetrahydrofuran compound of formula I.

Yet another aspect of the present invention is to provide a process for the preparation of tetrahydrofuran compound of formula A comprising the steps of:

a) reacting the compound of tetrahydrofuran compound formula I with a base to get the diol compound of formula D,
b) reacting the compound of formula D with tert-butyldimethylsilyl chloride to get diol protected compound of formula C,
c) dihydroxylating the compound of formula C to get a compound of formula B,
d) oxidizing the compound of formula B to get a tetrahydrofuran compound of formula A.

Yet another aspect of the present invention is using the tetrahydrofuran compounds of formula I and formula A in process for the preparation of Eribulin.

DETAILED DESCRIPTION OF THE INVENTION

The present invention is related to a process for the preparation of novel and stable intermediates of Eribulin and process for the preparation of the same.

One embodiment of the present invention provides a tetrahydrofuran compound of formula I.

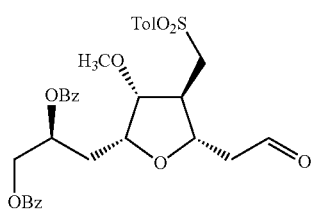

I

Another embodiment of the present invention provides a tetrahydrofuran compounds of formula X and XI.

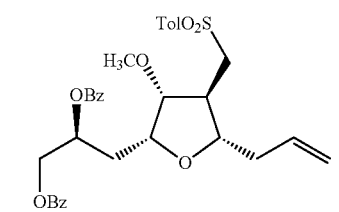

X

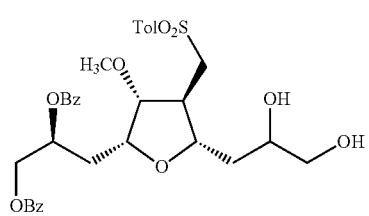

XI

Another embodiment of the present invention provides a tetrahydrofuran compounds of formula D and B.

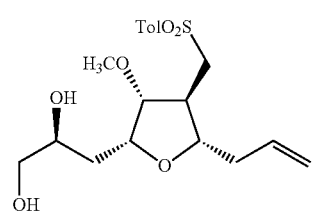

Compound-D

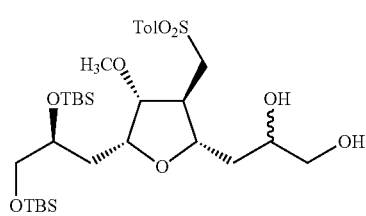

Compound-B

Yet another embodiment of the present invention is to provide a process for the preparation of a tetrahydrofuran compound of formula I comprising the steps of:

a) methylating a tetrahydrofuran compound of formula IX in presence of 1,8-Bis(dimethylamino)naphthalene to get a tetrahydrofuran compound of formula X,
b) dihydroxylating the tetrahydrofuran compound of formula X to get compound of formula XI,
c) oxidizing the compound of formula XI to get a tetrahydrofuran compound of formula I.

The invention according to above embodiments is shown in below scheme (Scheme-1).

Scheme-1

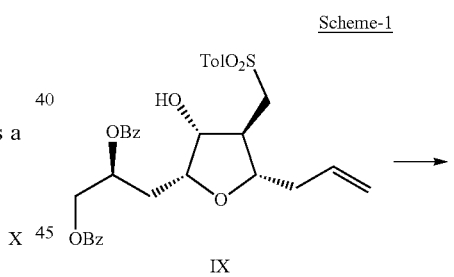

IX

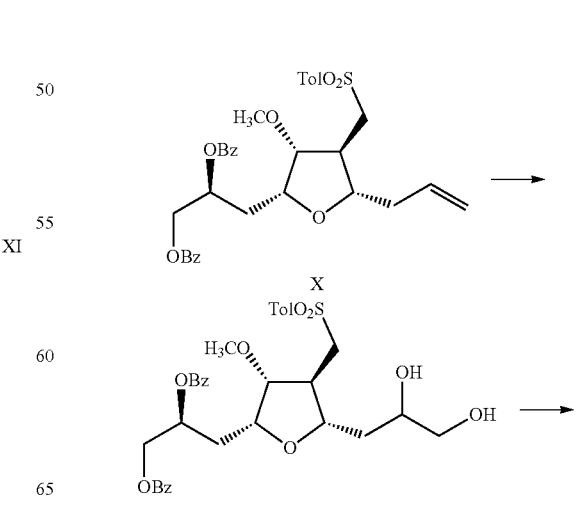

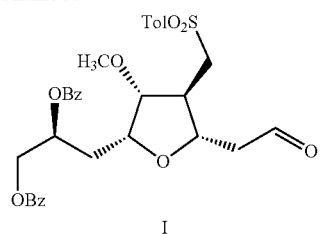

I

According to the present embodiment, methylating agent used in step a) is selected from, Methyl Iodide, Dimethyl sulfate, Methyl trifluoromethanesulfonate and Trimethyloxonium tetra fluoroborate, preferably Trimethyloxonium tetra fluoroborate.

According to the present embodiment, hydroxylation of compound of Formula (X) is carried out using osmium catalyst or dilute potassium permanganate ($KMnO_4$). A preferred osmium catalyst is osmium tetroxide ($OsO_4$). Optionally, a stoichiometric amount of an oxidant e.g. N-methylmorpholine oxide (NMO) or $K_3Fe(CN)_6$ is also employed.

According to the present embodiment, oxidation of compound of formula XI is carried out using oxidants like sodium periodate ($NaIO_4$) and lead tetraacetate [$Pb(OAc)_4$], preferably sodium periodate ($NaIO_4$).

The compound of formula (IX) used in the present invention is developed as per prior art process, which is as shown below (Scheme-2).

Scheme-2

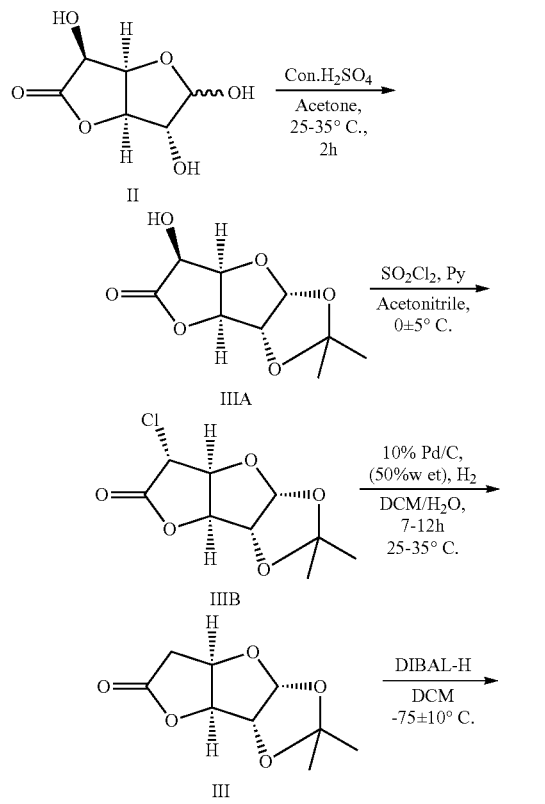

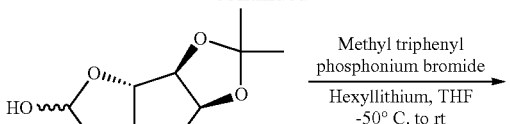

IVA

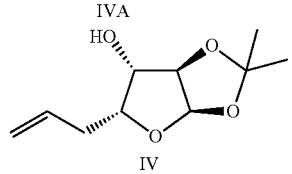

IV

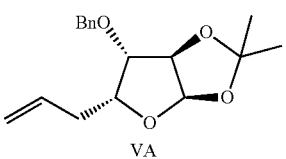

VA

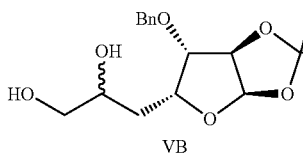

VB

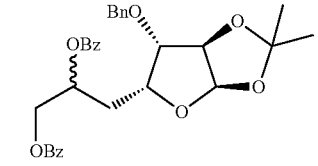

VC

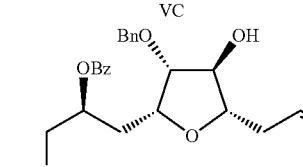

V

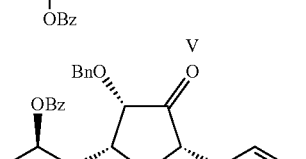

VI

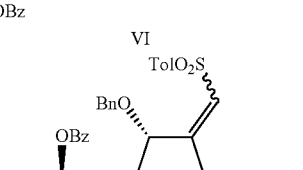

VII

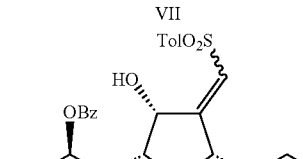

VIII

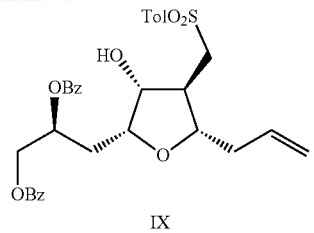

IX

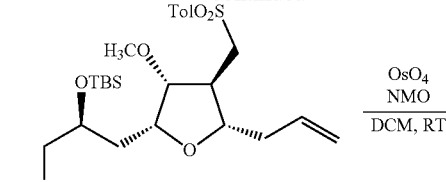

Compound-C

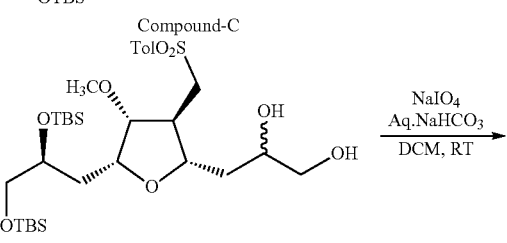

Compound-B

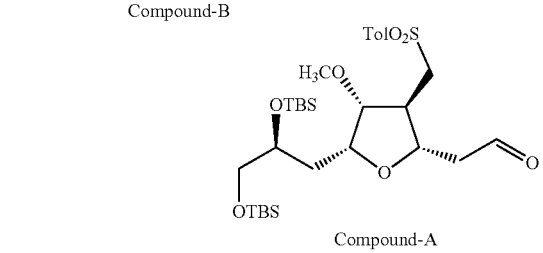

Compound-A

Yet another embodiment of the present invention is to provide a process for the preparation of tetrahydrofuran compound of formula A comprising the steps of:

a) reacting the compound of tetrahydrofuran compound formula I with a base to get the diol compound of formula D, b) reacting the compound of formula D with tert-butyldimethylsilyl chloride to get diol protected compound of formula C, c) dihydroxylating the compound of formula C to get a compound of formula B, d) oxidizing the compound of formula B to get a tetrahydrofuran compound of formula A.

According to the present embodiment, base employed in step a) is selected from potassium carbonate, sodium carbonate, preferably potassium carbonate.

According to the present embodiment, hydroxylation of compound of Formula C is carried out using osmium catalyst or dilute potassium permanganate ($KMnO_4$). A preferred osmium catalyst is osmium tetroxide ($OsO_4$). Optionally, a stoichiometric amount of an oxidant e.g. N-methylmorpholine oxide (NMO) or $K_3Fe(CN)_6$ is also employed.

According to the present embodiment, oxidation of compound of formula B is carried out using oxidants like sodium periodate ($NaIO_4$) and lead tetraacetate [$Pb(OAc)_4$], preferably sodium periodate ($NaIO_4$).

The conversion of compound of formula I to compound of formula A is shown in below scheme-3.

Yet another aspect of the present invention is using the compounds of formula I and formula A in process for the preparation of Eribulin.

Advantages of the Present Invention

1. Less expensive chemicals were used in the process.
2. Most of the reactions are taken insitu to subsequent stages without purification.
3. The conversion of diol to aldehyde is achieved using sodium metaperiodate instead of expensive reaction conditions of ozonolysis.

The Present invention is further illustrated in detail with reference to following examples. It is desired that the examples be considered in all respect as illustrative and are not intended to limit the scope of the invention in any way.

EXAMPLES

1) Preparation of Compound of Formula (III) 1,2-Di-O-isopropylidene-5-deoxy-α-D-xylo-hexofuranosidurono-6,3-lactone (III)

a) 1,2-,O-isopropylidene-α-D-glucurono-3,6-lactone (IIIA)

To a stirred solution of D-Glucuronolactone (100 g, 0.5677 mol) in acetone (1.0 L) under nitrogen atmosphere was added Conc.$H_2SO_4$ (55.68 g, 0.5677 mol) at 15±5° C. and stirred at 30±5° C. for 2-3 h. Reaction mass was quenched with solid sodium bicarbonate (500 g) and stirred for 2 h. Reaction mass was filtered and cake was washed with acetone (1.0 L). Filtrate was distilled off under reduced pressure and chased with dichloromethane (200 ml) to obtain crude mass. Dichloromethane (300 ml) was added to the above crude and stirred for 1 h. Precipitated solid was filtered and washed with dichloromethane (100 ml) and solvent from filtrate was distilled off under vacuum to obtain Scheme-3

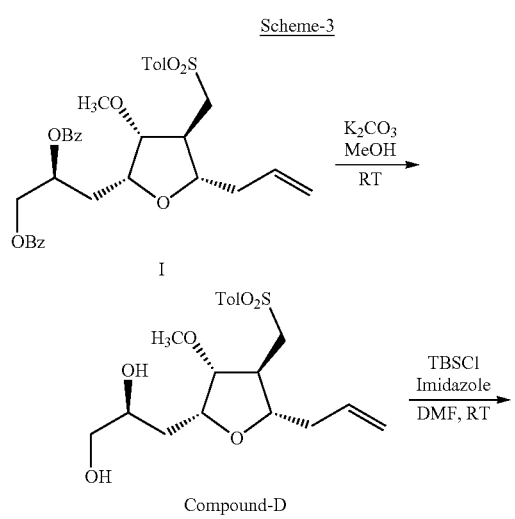

Compound-D the crude compound IIIA. This crude compound was dissolved in acetonitrile (300 ml) and distilled off solvent under vacuum to get compound IIIA as cream colored solid. The resulting crude was taken into acetonitrile (300 ml) and proceeded to next step.

b) 5-Chloro-5-deoxy-1,2-O-isopropylidene-β-L-idurono-6,3-lactone (IIIA)

To the above solution of IIIA, was added acetonitrile (440 ml) and pyridine (230 ml, 2.8385 mol) at 30±5° C. under nitrogen atmosphere. Reaction mass was cooled to −15±5° C. and Sulfuryl chloride (55.21 ml, 0.6812 mol) was added slowly while maintaining the reaction mass temperature at −15±5° C. Raised the reaction mass temperature to 0±5° C., over 30 min and stirred for 2 h at same temperature. Reaction progress was monitored by TLC. Reaction mass was quenched by pouring the mass into ice cold water (5-10° C., 3.5 L) and stirred for 60-90 min. Precipitated solid was filtered under suction with the help of water (600 ml). The wet cake was taken into ethyl acetate (1.2 L) and washed with water (2×600 ml). The combined aq. layer was extracted with ethyl acetate (600 ml). The combined organic layer was treated with activated charcoal (12 g), stirred for 1 h at 30±5° C. and filtered. Distilled off the solvent under reduced pressure and chased with isopropyl alcohol (200 ml) to obtain the crude IIIB compound. The crude IIIB compound was purified by leaching with Isopropyl alcohol (300 ml). Product was filtered and suck dried for 60 min and weight of the product: 110 g. The above compound was taken to next step.

Compound IIIB (108 g, 0.4603 mol) was taken in to dichloromethane (864 ml) and pyridine (48.2 ml, 0.5983 mol), 10% Pd/C (5.40 g) and water (21.6 ml) were added sequentially at 30±5° C. in autoclave. Cooled the reaction mass to 15±5° C. Applied the hydrogen pressure 70-80 psi at 15±5° C. and the temperature was raised to 25-30° C. Reaction mass was maintained for 10 h at 70-80 psi. Reaction progress was monitored by TLC. Reaction mass was transferred into a beaker with the help of water (540 ml) and filtered under suction using dichloromethane (540 ml). Layers were separated, dichloromethane layer was washed with water (540 ml) and separated layers. The solvent was distilled off under reduced pressure to obtain the crude compound III The above crude compound was leached from the solvent mixture of isopropyl alcohol (108 ml) and n-Heptane (432 ml) to obtain compound III as white colored solid. Weight of the product: 68.0 g, % of yield: 59.8 (over three steps).

$^1$H NMR (400 MHz, CDCl$_3$) δ 5.96-5.97 (1H, d, J=4.0 Hz), 4.98-5.00 (1H, m), 4.83-4.84 (1H, d, J=3.6 Hz), 4.81-4.82 (1H, d, J=3.2 Hz), 2.66-2.77 (2H, m), 1.51 (3H, s), 1.34 (3H, s).

$^{13}$C NMR (100 MHz, CDCl$_3$) δ 174.16, 112.74, 106.24, 85.50, 82.50, 78.01, 35.88, 26.97, 26.50. Mass (GC-MS): 185 [M-CH$_3$]$^+$, Purity (GC): >99%

2) Preparation of Compound of Formula IV (3aR, 5R,6S,6aR)-5-allyl-2,2-dimethyl-3a,5,6,6a-tetrahydrofuro[2,3-d][1,3]dioxol-6-ol (IV)

a) [3aR,4aR, 7aS, 7bR]2,2-Dimethyl perhydrofuro [2,3:4,5]furo[2,3-d][1,3]dioxol-6(R/S)-ol (IVA)

To a stirred solution of compound III (50 g, 0.2498 mol) in dichloromethane (1.0 L) under nitrogen atmosphere at −70±10° C. was added diisobutylaluminum hydride (DIBAL-H, 171 ml, 25% in toluene, 0.2996 mol) over 20-30 min Maintained the reaction mass for 1 h at same temperature, before being quenched with aq.potassium sodium tartarate solution (500 gr dissolved in 900 ml of water). Reaction mass was stirred and layers were separated. Aq.layer was extracted with dichloromethane (3×250 ml). The combined dichloromethane layers were dried over sodium sulphate (50 g) and distilled off the solvent under reduced pressure to result the crude compound IVA. Tetrahydrofuran (150 ml) was charged to the crude and distilled off solvent under vacuum to get compound of IVA as oily crude. Crude was dissolved in tetrahydrofuran (250 ml) to proceed next step.

To a stirred solution of methyltriphenylphosphonium bromide (267.70 g, 0.7493 mol) in tetrahydrofuran (1.0 L) at −15±5° C. was added n-hexyllithium (468.30 ml, 1.0M in hexane, 0.7493 mol) and temperature raised to 0±5° C. over 30 min and stirred for 1 h, followed by −45±5° C. over 2 h. Compound IVA in tetrahydrofuran (250 ml) was added slowly to the above mass, raised the mass temperature to 30±5° C. and maintained for 20 h, before being quenched with aq.ammonium chloride (200 gm dissolved in 800 ml of water) at 0±5° C. Methyl tert-butyl ether (1.0 L) was added to the above mass and separate the layers. The aq.layer extracted with methyl tert-butyl ether (3×500 ml) and combined organic layers were distilled off under reduced pressure to result the crude. The above crude compound was purified by silica gel column chromatography using ethyl acetate/hexane (5-20%) as eluent followed by leaching of the resulting crude with hexane to afford the pure compound IV as off-white colored solid.

Wt. of the compound: 24.1 g, % of yield: 48.2.

$^1$H NMR (400 MHz, CDCl$_3$) δ 5.90-5.91 (1H, d, J=4.0 Hz), 5.80-5.89 (1H, m), 5.17-5.23 (1H, m), 5.10-5.13 (1H, m), 4.51-4.52 (1H, d, J=3.6 Hz), 4.17-4.22 (1H, m), 4.09 (1H, m), 2.50-2.57 (1H, m), 2.38-2.46 (1H, m), 1.67-1.68 (1H, d, J=6.0 Hz), 1.50 (3H, s), 1.31 (3H, s).

$^{13}$C NMR (100 MHz, CDCl$_3$) δ 133.69, 117.58, 111.43, 104.31, 85.13, 79.49, 75.14, 32.24, 26.53, 26.07. Mass (GC-MS): 185 [M-CH$_3$]$^+$, Purity (GC): >99%

3) Preparation of Compound of Formula (V) [(2S)-3-[(2R,3R,4S,5S)-5-allyl-3-benzyloxy-4-hydroxy-tetrahydrofuran-2-yl]-2-benzoyloxy-propyl] benzoate (V)

a) (3aR,5R,6S,6aR)-5-allyl-6-benzyloxy-2,2-dimethyl-3a,5,6,6a-tetrahydrofuro[2,3-d][1,3]dioxole (VA)

Potassium tert-butoxide (72.84 g, 0.6492 mol) in tetrahydrofuran (600 ml) at −12.5±2.5° C. was added compound IV in tetrahydrofuran (100 g of compound-IV was dissolved in 400 ml tetrahydrofuran, 0.4994 mol) and stirred the mass for 30-40 min at same temperature. Benzyl bromide (71.26 ml, 0.5992 mol) was added slowly to the above mass and stir for 30-40 min Raised the mass temperature to 30±5° C. and maintain for 60-90 min Reaction mass was quenched with aq ammonium chloride (40 g of NH$_4$Cl was dissolved in 360 ml of water), extracted with toluene (3×500 ml). The combined toluene layers were washed with brine solution (50 g of NaCl was dissolved in 450 ml of water) and layers were separated. Distilled off the solvent under reduced pressure to obtain compound VA as brown colored oily mass. Weight of the oil: 145 g.

b) 3-[(3aR,5R,6S,6aR)-6-benzyloxy-2,2-dimethyl-3a,5,6,6a-tetrahydrofuro[2,3-d][1,3]dioxol-5-yl]propane-1,2-diol (VB)

To a stirred solution of tert-butanol (1885 ml), potassium hexacyanoferrate (III) (509.6 g, 1.5478 mol), potassium carbonate (217.34 g, 0.5727 mol), (DHQ)$_2$AQN (1.92 g, 0.00224 mol) and water (2610 ml) was added to VA in tert-butanol (VA crude (145 g) was dissolved in tert-butanol (725.0 ml)) at 30±5° C. Reaction mass cooled to 2.5±2.5° C. and potassium osmate dihydrate (0.46 g, 0.00124 mol) was added. Reaction mass was maintained for 15-16 h under stirring before quenched with sodium sulphite (220 g). Mass was allowed to 30±5° C., water (600 ml) and ethyl acetate (2100 ml) were charged. Layers were separated, aq. layer was extracted with ethyl acetate (1×1400 ml, and 1×700 ml). The combined organic layer was washed with brine solution (72 g of NaCl was dissolved in 650 ml of water) and distilled off the solvent under reduced pressure to obtain the brown colored oily mass (VB). Toluene (300 ml) was added to the oily mass and distilled off the solvent under vacuum to give compound of VB as brown colored oily mass. Weight of the oily mass: 161.98 g (Theoretical yield). The oily mass was taken to next step without purification.

c) [3-[(3aR,5R,6S,6aR)-6-benzyloxy-2,2-dimethyl-3a,5,6,6a-tetrahydrofuro[2,3-d [1,3] dioxol-5-yl]-2-benzoyloxy-propyl] benzoate (VC)

To a stirred solution of VB (161.98 g, 0.4993 mol) in toluene (2430 ml), aq.sodium hydroxide solution (440.0 g of NaOH was dissolved in 1134.0 ml of water) and tetrabutylammonium bromide (1.60 g, 0.00499 mol) at 2.5±2.5° C. was added benzoyl chloride (175.40 g, 1.2482 mol). Reaction mass was stirred for 30-40 min, at same temperature and then allowed to 30±5° C. Maintained the mass for 60-90 min. Water (1620 ml) was added to the reaction mass and extracted with toluene (2×500 ml). Combined organic layer was washed with water (810 ml) and layers were separated. Organic layer was treated with activated charcoal (16.2 g) and filtered. The filtrate was dried over anhydrous sodium sulphate (40 g) and taken to next step.

Titanium isopropoxide (170.29 g, 0.5991 mol) was added to the stirred solution of titanium tetrachloride (340.93 g, 1.7974 mol) in toluene (1862 ml) at 2.5±2.5° C. Reaction mass temperature was raised to 12.5±2.5° C. and stirred for 45-60 min, during which reaction mass becomes cream color suspension. Toluene layer of VC along with allyltrimethylsilane (273.83 g, 2.3966 mol) was added to the above suspension at 10-15° C., temperature was raised to 30±5° C. and stirred for 60-90 min. After completion of reaction by TLC, reaction mass was quenched with dilute aq.hydrochloric acid at 2.5±2.5° C. (133 ml of conc. hydrochloric acid was dissolved in 1200 ml of water). Reaction mass was extracted with toluene (2×1330 ml) and combined toluene layer was washed with brine (133 g of sodium chloride was dissolved in 1200 ml of water). Distilled off the toluene under vacuum at 50-55° C. to obtain pale brown color solid, which was purified by precipitation method from the solvent mixture of ethyl acetate and hexane to afford compound V as white colored solid. Wt. of the compound: 144 g, % of yield: 55.8.

$^1$H NMR (400 MHz, CDCl$_3$) δ 8.04 (2H, m), 7.98 (2H, m), 7.54 (2H, m), 7.28-7.45 (9H, m), 5.80-5.82 (1H, m), 5.59-5.61 (1H, m), 5.1 (1H, dt, J=17.0, 2.0 Hz), 5.05 (1H, dt, J=10.4, 1.2 Hz), 4.68 (1H, d, J=11.6 Hz), 4.58 (1H, d, J=11.6 Hz), 4.57 (1H, s), 4.52-4.53 (1H, d, J=2.0 Hz), 4.17 (1H, m), 4.0 (1H, m), 3.9 (1H, dd, J=4.8, 2.0 Hz), 3.65 (1H, m), 2.12-2.48 (2H, m), 2.25 (2H, t, J=6.4 Hz), 1.74 (1H, d, J=4.0 Hz); $^{13}$C NMR (100 MHz, CDCl$_3$) δ 166.22, 166.14, 166.1, 137.83, 134.27, 134.23, 133.05, 130.01, 129.72, 129.66, 128.50, 128.35, 127.87, 127.73, 117.5, 85.9, 84.16, 84.1, 79.77, 79.67, 76.80, 71.75, 70.15, 70.10, 65.84, 37.95, 30.76

Mass (LC-MS): 534.20 [M+NH$_4$]$^+$, Purity (HPLC): >98%

4) Preparation of Compound of Formula (X)[(2S)-3-[(2R,3R,4R,5S)-5-allyl-3-hydroxy-4-(p-tolylsulfonylmethyl)tetrahydrofuran-2-yl]-2-benzoyloxy-propyl] benzoate (X)

a) [(2S)-3-[(2R,3S,5S)-5-allyl-3-benzyloxy-4-oxo-tetrahydrofuran-2-yl]-2-benzoyloxy-propyl] benzoate (VI)

To a stirred solution of compound of V (30 g, 0.058 mol) in dichloromethane (600 ml) at 30±5° C. was added sodium bicarbonate (14.62 g, 0.174 mol) and DessMartin periodinane (36.90 g, 0.087 mol). Reaction mass was stirred for 3-5 h then quenched with aq.sodium thiosulphate (150.0 g of sodium thiosulphate was dissolved in 150.0 ml of water) at 10±5° C. Water (300 ml) was added to the above reaction mass at 30±5° C. and layers were separated. Aq.layer was extracted with dichloromethane (2×90 ml) and the combined dichloromethane layer was washed with brine (15.0 g of sodium chloride was dissolved in 135.0 ml of water). Solvent was distilled off under reduced pressure to result oily compound. Crude compound was purified by silicagel column chromatography using ethyl acetate/hexane as eluent to afford pure compound VI as pale yellow oil. Wt. of the oil: 26.60 g, % of yield 89.0.

b)[(2S)-3-[(2R,3R,4Z,5S)-5-allyl-3-benzyloxy-4-(p-tolylsulfonylmethylene)tetrahydrofuran-2-yl]-2-benzoyloxy-propyl] benzoate (VII)

1-(Diethoxyphosphorylmethylsulfonyl)-4-methyl-benzene (35.20 g, 0.1149 mol) in toluene (1183.0 ml) at 0±5° C. was added LiHMDS (112.50 ml, 1.06 M solution in THF/ethylbenzene) through addition funnel over 30 min and maintained the mass temperature at 0±5° C. Mass temperature was raised to 30±5° C. and stirred for 45-60 min. Reaction mass was cooled to 0±5° C. and compound VI (43.80 g (0.08512 mol) in toluene of (307.0 ml) was added through addition funnel. Reaction mass temperature was raised to 30±5° C. over 60-90 min and stirred for 10-12 h. Aq.ammonium chloride (219.0 g of ammonium chloride was dissolved in 876.0 ml of water) was added to the reaction mass at 0±5° C. Mass temperature was raised to 30±5° C. and layers were separated. Aq.layer was extracted with toluene (1×438 ml, 1×219 ml). The combined organic layer was washed with brine and solvent was distilled off under reduced pressure to get the oily crude compound VII, which was purified by silicagel column chromatography using ethyl acetate/hexane as eluent to get the compound VII as pale yellow colored oil. Wt. of the oil: 42.06 g, % of yield 79.2.

c) [(2S)-3-[(2R,3R,4E,5S)-5-allyl-3-hydroxy-4-(p-tolylsulfonylmethylene)tetrahydrofuran-2-yl]-2-benzoyloxy-propyl] benzoate ((VII)

To a stirred solution of compound VII (80 g, 0.1199 mol) in dichloromethane (1600 ml) was added pentamethylbenzene (106.65 g, 0.7194 mol) and cooled to −70±10° C. Boron trichloride (360 ml, 1.0M in dichloromethane, 0.3597 mol) was added slowly while maintaining the reaction mass temperature at −70±10° C. and then maintained for 3-5 h at same temperature. After reaction completed by TLC, reaction mass was quenched with a solvent mixture of dichloromethane and methanol (908 ml of dichloromethane and 160 ml of methanol) by adding solvent mixture through addition funnel while maintaining the temperature −70±10° C. Then reaction mass was stirred for 30 min then mass temperature was raised to 0±5° C. followed by 30±5° C. and stirred for 30-45 min. Water (800 ml) was added to the above mass and layers were separated. Dichloromethane layer was washed with water (800 ml) and layers were separated. The combined aq.layer was extracted with dichloromethane (2×800 ml) and layers were separated. Solvent was distilled off under reduced pressure and the resulting crude compound was purified by silica gel column chromatography using ethyl acetate/hexane as eluents to afford oily compound of VIII Wt. of the compound: 57.6 g, % of yield: 83.2.

d) [(2S)-3-[(2R,3R,4R,5S)-5-allyl-3-hydroxy-4-methyl-tetrahydrofuran-2-yl]-2-benzoyloxy-propyl] benzoate; 1-methyl-4-methylsulfonyl-benzene (IX)

To the suspension of sodium triacetoxy borohydride (94.80 g, 0.4473 mol) in toluene (344 ml) and 1,2-DME (688 ml) in 3.0 L 3N RB flask was added tetrabutylammonium chloride (82.87 g, 0.2982 mol) under nitrogen atmosphere. Reaction mass temperature was raised to 60-65° C. and stirred for 60-90 min to get white color suspension. Reaction mass was cooled to 45±5° C. and compound VIII (86 g, 0.1491 mol) in toluene (344 ml) was added slowly. Then the reaction mass temperature was raised to 75-80° C. and stirred for 3-5 h. After completion of reaction by TLC reaction mass was quenched with water (688 ml). Layers were separated and aq.layer was extracted with toluene (2×430 ml). The combined organic layer was washed with aq. sodium bicarbonate (2×473 ml, 86.0 g of NaHCO₃ dissolved in 860 ml of water) and brine (43.0 g sodium chloride was dissolved in 430 ml of water). Layers were separated and solvent was distilled off under reduced pressure to obtain the crude compound which was purified by silicagel column chromatography using ethyl acetate/hexane as eluent to afford compound IX as yellow coloured syrup. Wt. of the compound: 68.7 g, % of yield: 79.6.

To a stirred solution of compound IX (67 g, 0.1158 mol) in dichloromethane (800 ml) was added 1,8-Bis(dimethylamino)naphthalene (86.79 g, 0.405 mol), trimethyloxonium tetrafluoroborate (54.72 g, 0.37 mol) at 30±5° C. Heterogeneous reaction mass was stirred for 20 h and reaction progress was monitored by TLC. Reaction mass was filtered under suction and filtered cake was washed with dichloromethane (670.0 ml). Filtrate was washed with dilute aq.hydrochloric acid (2×670 ml) (prepared from conc. hydrochloric acid 67.0 ml dissolved in water 603 ml). The combined aq.layer was extracted with dichloromethane (2×335 ml) and layers were separated. Organic layer was washed with water (670 ml) and layers were separated. Then solvent was distilled off under reduced pressure to get the crude compound which was purified by silicagel column chromatography using ethyl acetate/hexane as eluent to afford compound X as reddish brown viscous oil. Wt. of the oil: 60 g, % of yield: 87.4.

¹H NMR (400 MHz, CDCl₃) δ 7.99-8.05 (4H, m), 7.77-7.79 (2H, d, J=8.0 Hz), 7.52-7.55 (2H, m), 7.35-7.44 (6H, m), 5.58-5.68 (2H, m), 4.92-5.00 (2H, m), 4.55-4.56 (2H, d, J=5.2 Hz), 3.85-3.88 (2H, m), 3.50-3.54 (1H, m), 3.39 (3H, s), 2.97-3.10 (2H, dd, J=14.0, 8.4 Hz), 2.47-2.51 (1H, m), 2.45 (3H, s), 2.23-2.36 (4H, m); ¹³C NMR (100 MHz, CDCl₃) δ 166.21, 166.05, 145.01, 136.43, 133.92, 133.06, 129.71, 129.65, 129.00, 128.35, 128.35, 128.19, 127.94, 117.52, 86.18, 83.31, 78.01, 70.26, 65.66, 58.18, 57.34, 43.09, 39.37, 30.28, 21.62. Mass (ES): 610.2 [M+NH4]⁺, Purity (HPLC): >97%

5) Preparation of Compound of Formula (I) [(2S)-2-benzoyloxy-3-[(2R,3R,4S,5S)-3-methoxy-5-(2-oxoethyl)-4-(p-tolylsulfonylmethyl)tetrahydrofuran-2-yl]propyl]benzoate (I)

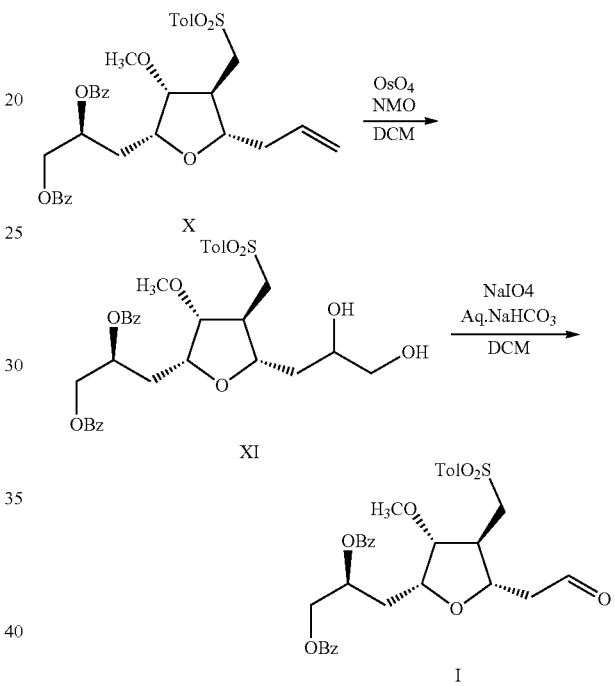

a) [(2S)-2-benzoyloxy-3-[(2R,3R,4S,5S)-5-(2,3-dihydroxypropyl)-3-methoxy-4-(p-tolylsulfonylmethyl)tetrahydrofuran-2-yl]propyl] benzoate (XI)

To a stirred solution of compound X (3.0 g, 5.06 mmol) in dichloromethane (30 ml) was added NMO (50% water, 1.57 ml, 15.18 mmol) followed by osmium tetroxide (4 wt % in water, 0.63 ml, 0.101 mmol) at 30±5° C. Reaction mass was maintained for 2-3 h and reaction progress was monitored by TLC. Reaction mass was quenched with 10% aq.sodium thiosulphate solution (30 ml) (3.0 g of sodium thiosulphate was dissolved in 27 ml of water) and layers were separated. Aq.layer was extracted with dichloromethane (3×30 ml). Combined dichloromethane layer was distilled off under reduced pressure to give crude compound which was purified by silicagel column chromatography using ethyl acetate/hexane as eluent to obtain compound XI as brown coloured viscous oil. Wt. of the oil: 2.8 g, % of yield: 88.0.

Compound XI (2.4 g, 3.83 mmol) in dichloromethane (48.0 ml) at 30±5° C. was added sodium metaperiodate in 5 lots (1×2.45 g, 4×1.22 g) while monitoring the reaction progress by TLC. After reaction completion reaction mass was filtered under suction using dichloromethane (50 ml) and filtrate was washed with water (20 ml). Dichloromethane layer was dried over sodium sulphate (5.0 g) and solvent was distilled off under reduced pressure to afford compound I as brown coloured viscous oil. Wt. of the oil: 2.2 g, % of yield: 96.6.

$^1$H NMR (400 MHz, CDCl$_3$) δ 9.65 (1H, s), 7.99-8.04 (4H, m), 7.80 (2H, d, J=8.4 Hz), 7.54-7.58 (2H, m), 7.39-7.46 (6H, m), 5.56-5.59 (1H, m), 4.57 (1H, dt, J=7.6 Hz), 4.05 (1H, m), 3.94 (1H, m), 3.87-3.88 (1H, dd, J=4.0, 1.2 Hz), 3.37 (3H, s), 3.23-3.28 (1H, dd, J=14.4 Hz, 6.4 Hz) 2.83 (2H, m), 2.55 (1H, q, J=6.4 Hz, 1.6 Hz), 2.46 (3H, s), 2.21-2.26 (2H, m); $^{13}$C NMR (100 MHz, CDCl$_3$) δ 200.37, 166.13, 166.01, 145.11, 136.27, 133.10, 133.07, 130.03, 129.87, 129.64, 129.60, 128.34, 127.83, 86.02, 78.54, 78.06, 70.09, 65.51, 57.84, 57.22, 43.76, 30.36, 21.59; Mass (ES): 612.18 [M+NH4]$^+$. Purity (HPLC): >96%.

6) Preparation of 2-[(2S,3S,4R,5R)-5-[(2S)-2,3-bis[[tert-butyl(dimethyl)silyl]oxy]propyl]-4-methoxy-3-(p-tolylsulfonylmethyl)tetrahydrofuran-2-yl]acetaldehyde (Compound A)

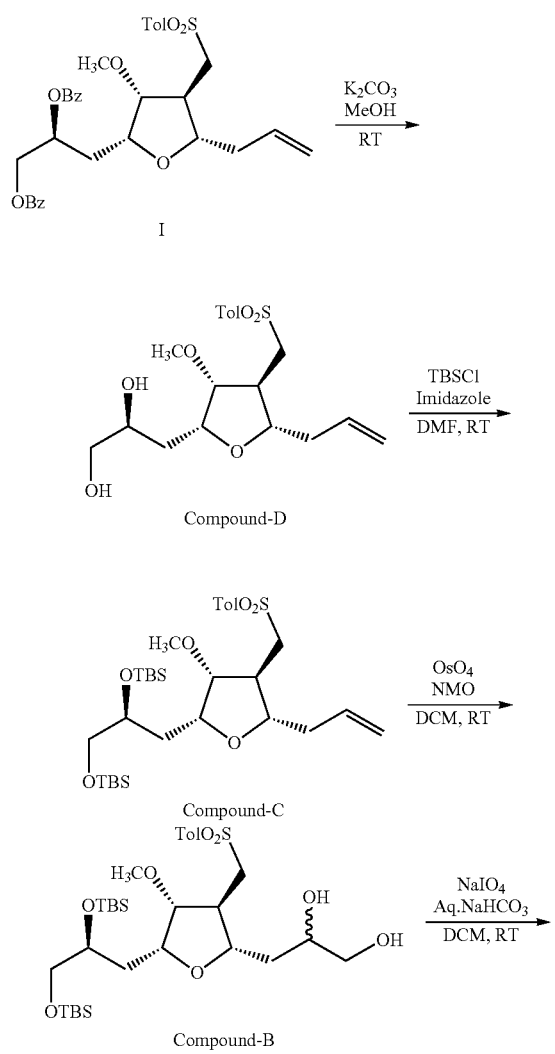

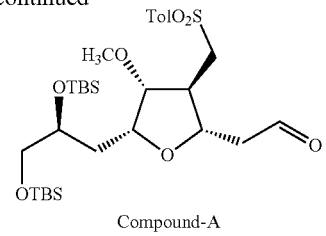

Compound-A a) (2S)-3-[(2R,3R,4S,5S)-5-allyl-3-methoxy-4-(p-tolylsulfonylmethyl) tetrahydrofuran-2-yl] propane-1, 2-diol (Compound-D)

To a solution of compound-I (10.0 g, 0.0168 mol) in methanol (70.0 ml) at 30±5° C. was added potassium carbonate (1.63 g, 0.01176 mol) and mass stirred for 60-90 min. After completion of reaction as indicated by TLC, the reaction mass was quenched with acetic acid (0.83 g, 0.0139 mol). The above mass was adsorbed on silica gel (60-120 mesh, 30 g) and purified by silica gel column (60-120 mesh, 50 g) chromatography using 20% ethyl acetate in hexane to ethyl acetate and 5% methanol in ethyl acetate as eluent. The pure column fractions were concentrated in vacuo to result the Compound-D as oily mass. Wt. of the oil: 5.50 g, % of yield: 84.87.

b) [(2S)-3-[(2R,3R,4S,5S)-5-allyl-3-methoxy-4-(p-tolylsulfonylmethyl) tetrahydrofuran-2-yl]-2-[tert-butyl (dimethyl) silyl] oxy-propoxy]-tert-butyl-dimethyl-silane (Compound-C)

To a stirred solution of compound Compound-D (5.50 g, 0.0143 mol) in N,N-dimethylformamide (22 ml) was added imidazole (4.86 g, 0.0715 mol) and tert-butyldimethylsilyl chloride (6.45 g, 0.0429 mol) under nitrogen atmosphere at 25-30° C. Reaction mass was stirred for 20 hours and diluted with methyl tert-butyl ether (55.0 ml). The reaction mass was stirred for 30 min and water (110.0 ml) was added. Then layers were separated.

Aq.layer was extracted with methyl tert-butyl ether (2×27.5 ml) and layers were separated. Organic layers were combined and was washed with water (2×27.5 ml). The methyl tert-butyl ether layer was concentrated in vacuo to result the pale brown colored oily mass of Compound-C. Wt. of the oil: 9.1 g, % of yield: Quantitative. The oily mass was taken to next step without purification.

c) 3-[(2S,3S,4R,5R)-5-[(2S)-2,3-bis[[tert-butyl(dimethyl)silyl]oxy]propyl]-4-methoxy-3-(p-tolylsulfonylmethyl)tetrahydrofuran-2-yl]propane-1,2-diol (Compound-B)

To the solution of Compound-C (9.0 g, 0.0146 mol) in methylene dichloride (90 ml) was added N-methylmorpholine N-oxide (6.05 ml, 0.0292 mol) and osmium tetroxide (1.40 ml, 4% wt in water) at 25-30° C. and stirred the resulting reaction mass for 2-3 hours. After completion of reaction by TLC, reaction mass was quenched with 10% aq.sodium thiosulphate (90 ml, 9.0 g of sodium thiosulphate was dissolved in 81.0 ml of water) and stirred for 30 min. Layers were separated and aq.layer was extracted with methylene dichloride (2×90.0 ml) and the organic layer was washed with water (45.0 ml). Organic layers were combined and concentrated in vacuo to get crude material of Compound-B. Crude material was purified by silicagel (60-120 mesh) column chromatography, using ethyl acetate/hexane to ethyl acetate as eluent to afford Compound-B as brown coloured thick mass. Wt. of the compound: 6.5 g, % of yield: 68.6.

$^1$H NMR (400 MHz, CDCl$_3$) δ 7.72-7.70 (2H, d, J=7.6 Hz), 7.32-7.30 (2H, d, J=7.6 Hz), 3.88-3.77 (2H, m), 3.69-3.65 (3H, m), 3.56-3.46 (2H, m), 3.41-3.36 (2H, m), 3.31 (3H, s), 3.01-2.98 (2H, m), 2.80-2.79 (1H, J=4.4 Hz), 2.49-2.47 (1H, m), 2.39 (3H, s), 2.20-2.17 (1H, t, J=6.0 Hz), 1.92-1.89 (1H, m), 1.82-1.70 (2H, m), 1.66-1.60 (1H, m), 0.80 (9H, s), 0.79 (9H, s), −0.037 (3H, s), −0.03 (3H, s), −0.007 (6H, s); $^{13}$C NMR (100 MHz, CDCl$_3$) δ 145.11, 136.42, 130.09, 127.83, 85.86, 82.39, 78.85, 71.11, 70.72, 67.66, 66.62, 58.19, 57.37, 44.34, 37.98, 33.32, 25.93, 25.86, 21.62, 18.32, 18.10, −4.20, −5.37. Mass (ES): 647.02 [M+H]$^+$, Purity (HPLC): >95% d) 2-[(2S,3S,4R,5R)-5-[(2S)-2,3-bis[[tert-butyl(dimethyl)silyl]oxy]propyl]-4-methoxy-3-(p-tolylsulfonylmethyl)tetrahydrofuran-2-yl]acetaldehyde (Compound-A)

To the solution of Compound-B (5.0 g, 0.0077 mol) in ethyl acetate (75 ml) was added saturated aq.sodium bicarbonate (15.0 ml) solution and water (35.0 ml). The mass becomes biphasic solution. Sodium metaperiodate was added in 4 lots (14.82 g, 2×3 mol and 2×1.5 mol) in 1-2 hours intervals. Reaction mass was stirred for 2 h at 25-35° C. After completion of reaction as indicated by TLC, reaction mass was filtered under suction and washed with ethyl acetate (2×50 ml). Layers were separated and aq. sodium thiosulphate (2×50.0 ml) was added to the ethyl acetate layer and stirred for 10-20 min. Organic layer was separated and washed with saturated aq.sodium bicarbonate solution (2×50.0 ml) and water (2×50.0 ml). Layers were separated and solvent was distilled off from organic layer under vacuum and the resulting crude mass was chased with toluene, to afford the Compound-A as pale brown colored thick oily mass.

Wt. of the compound: 4.1 g, % of yield: 86.31.

We claim:

1. A tetrahydrofuran compound represented by any one of formulae I, XI, and B:

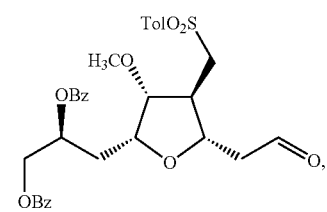

I

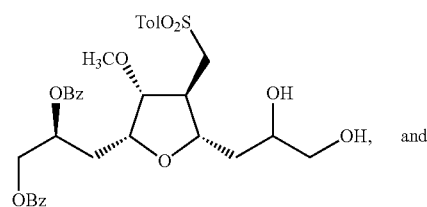

XI

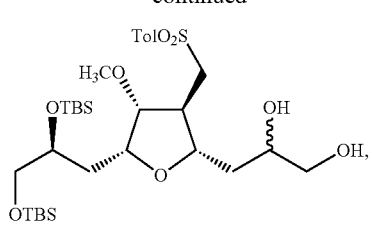

B wherein Bz represents

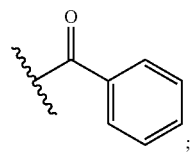 [SMILES: *C(=O)c1ccccc1]

;

Tol represents

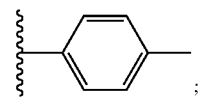

;

and TBS represents

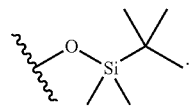 [SMILES: *O[Si](C)(C)C(C)(C)C]

.

2. A process for the preparation of a tetrahydrofuran compound of formula I:

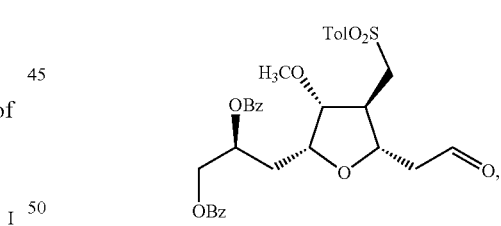

I comprising the steps of:
a) methylating a tetrahydrofuran compound of formula IX:

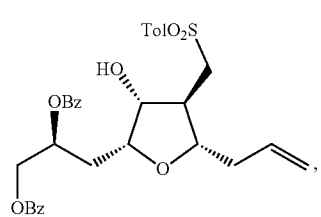

IX in presence of 1,8-Bis(dimethylamino)naphthalene to get a tetrahydrofuran compound of formula X;

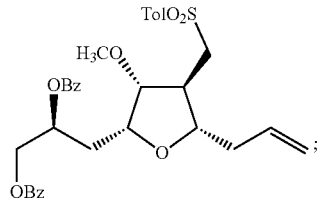

b) dihydroxylating the tetrahydrofuran compound of formula X to get a compound of formula XI;

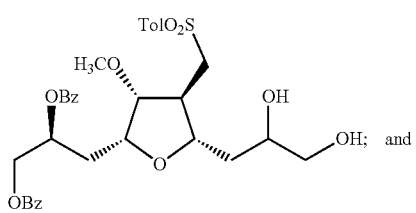

c) oxidizing the compound of formula XI to get the tetrahydrofuran compound of formula I, wherein Bz represents

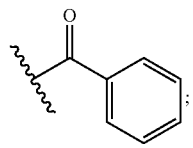 [SMILES: *C(=O)c1ccccc1]

and Tol represent

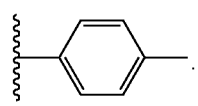 [SMILES: *c1ccc(C)cc1]

3. The process according to claim 2, wherein the methylating agent used in step a) is selected from Methyl Iodide, Dimethyl sulfate, Methyl trifluoromethanesulfonate and Trimethyloxonium tetra fluoroborate.

4. The process according to claim 2, wherein the hydroxylation of the compound of formula X in step b) is carried out using osmium tetroxide ($OsO_4$) or dilute potassium permanganate ($KMnO_4$).

5. The process according to claim 2, wherein, in the hydroxylation of the compound of formula X in step b), a stoichiometric amount of an oxidant N-methylmorpholine oxide (NMO) or $K_3Fe(CN)_6$ is used.

6. The process according to claim 2, wherein the oxidizing reagent is selected from sodium periodate ($NaIO_4$) and lead tetraacetate [$Pb(OAc)_4$].

7. A process for the preparation of a tetrahydrofuran compound of formula A:

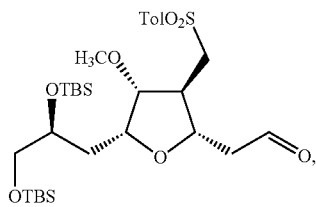

comprising the steps of:
a) reacting a tetrahydrofuran compound of formula I-b:

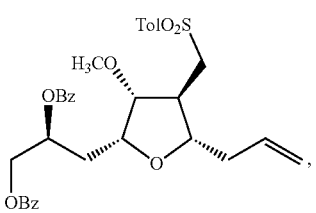

with a base to get a diol compound of formula D;

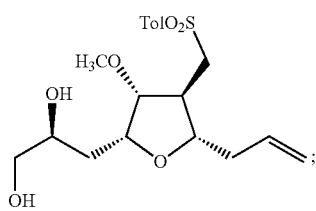

b) reacting the compound of formula D with tert-butyldimethylsilyl chloride to get a diol protected compound of formula C;

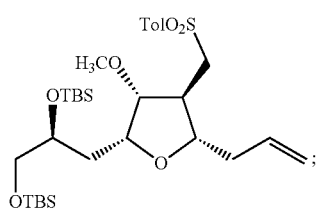

c) dihydroxylating the compound of formula C to get a compound of formula B:

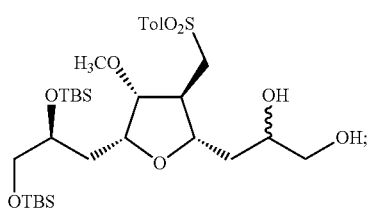

d) oxidizing the compound of formula B to get the tetrahydrofuran compound of formula A, wherein Bz represents

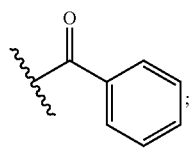 [SMILES: *C(=O)c1ccccc1]

Tol represents

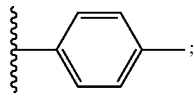

and TBS represents

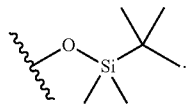 [SMILES: *O[Si](C)(C)C(C)(C)C]

8. The process according to claim 7, wherein the base employed in step a) is selected from potassium carbonate and sodium carbonate.

9. The process according to claim 7, wherein the hydroxylation of the compound of formula C in step c) is carried out using osmium tetroxide ($OsO_4$) or dilute potassium permanganate ($KMnO_4$).

10. The process according to claim 7, wherein the oxidizing reagent is selected from sodium periodate ($NaIO_4$) and lead tetraacetate [$Pb(OAc)_4$].

* * * * *